US005716805A

United States Patent [19]
Srinivasan et al.

[11] Patent Number: 5,716,805
[45] Date of Patent: Feb. 10, 1998

[54] METHODS OF PREPARING SOLUBLE, OLIGOMERIC PROTEINS

[75] Inventors: Subhashini Srinivasan, Kirkland; Melanie K. Spriggs, Seattle, both of Wash.

[73] Assignee: Immunex Corporation, Seattle, Wash.

[21] Appl. No.: 446,922

[22] Filed: May 18, 1995

Related U.S. Application Data

[63] Continuation-in-part of Ser. No. 107,353, Aug. 13, 1993, abandoned, which is a continuation-in-part of Ser. No. 969,703, Oct. 23, 1992, abandoned, which is a continuation-in-part of Ser. No. 805,723, Dec. 5, 1991, abandoned, which is a continuation-in-part of Ser. No. 783,707, Oct. 25, 1991, abandoned.

[51] Int. Cl.$^6$ .......................... C12N 15/00; C07K 14/705
[52] U.S. Cl. .......................... 435/69.1; 435/69.7; 435/70.1; 435/71.1; 435/172.3; 435/7.2; 435/320.1; 435/252.3; 435/325; 530/350; 536/23.1; 536/23.5
[58] Field of Search ........................ 435/69.7, 252.3, 435/240.2, 320.1, 70.1; 530/350; 935/10; 536/23.4, 23.5

[56] References Cited

U.S. PATENT DOCUMENTS

| 5,073,627 | 12/1991 | Curtis et al. | 530/351 |
|---|---|---|---|
| 5,155,027 | 10/1992 | Sledziewski et al. | 435/69.7 |

FOREIGN PATENT DOCUMENTS

| A0325224 | 7/1989 | European Pat. Off. . | |
| WO 93/08207 | 4/1993 | WIPO . | |
| WO 93/11162 | 6/1993 | WIPO . | |
| WO 93/19176 | 9/1993 | WIPO . | |
| WO 93/23550 | 11/1993 | WIPO . | |

OTHER PUBLICATIONS

DeLano and Brunger, Proteins 20(2): 105, 1994.
Sorger and Nelson, Cell 59: 807, 1989.
Reid et al, J. Biol. Chem. 263(16): 7753, 1988.
Wilcox et al, Biochemistry 31: 10458, 1992.
Rust et al, Arch. Biochem. Biophys. 290: 116, 1991.
Lu et al, Biochem. J. 284:795, 1992.
Crouch et al, J. Biol. Chem. 268: 2976, 1993.
Kostelny et al., *J. Immunol.* 148:1547, 1992.
Hu et al., *Science* 250:1400, 1990.
Blondel and Bedouille, *Protein Engineering* 4:457, 1991.
Zhu et al., *Protein Science* 2:383, 1993.
Alber, Sixth Symposium of the Protein Society, San Diego, CA.
Pack and Plückthun, *Biochemistry* 31:1579, 1992.
Harbury et al., *Science* 262:1401, 1993.
Hollenbaugh et al., Unit 10.19 in *Current Protocols in Immunology*, 1992.
Hoppe, et al., *FEBS Letters* 344:191, 1994.

*Primary Examiner*—Stephen Walsh
*Assistant Examiner*—Eliane Lazar-Wesley
*Attorney, Agent, or Firm*—Patricia Anne Perkins

[57] ABSTRACT

There is disclosed a method of preparing a soluble mammalian protein by culturing a host cell transformed or transfected with an expression vector encoding a fusion protein comprising a zipper domain and a heterologous mammalian protein.

15 Claims, 2 Drawing Sheets

METHODS OF PREPARING SOLUBLE, OLIGOMERIC PROTEINS

CROSS REFERENCE TO RELATED APPLICATION

This application is a continuation-in-part application of U.S. patent application Ser. No. 08/107,353, filed Aug. 13, 1993, now abandoned, which is a continuation-in-part of U.S. patent application Ser. No. 07/969,703, filed Oct. 23, 1992, now abandoned, which is a continuation-in-part of U.S. patent application Ser. No. 07/805,723, filed on Dec. 5, 1991, now abandoned, which is a continuation-in-part of U.S. patent application Ser. No. 07/783,707, filed on Oct. 25, 1991, now abandoned.

TECHNICAL FIELD OF THE INVENTION

The present invention relates to a method of preparing soluble oligomeric proteins using recombinant DNA technology.

BACKGROUND OF THE INVENTION

The biological activity of proteins is dependent upon proper tertiary and quaternary structure, or conformation. Many proteins exists as oligomers (structures comprised of two or more polypeptide chains) in their native form. Such oligomers are often stabilized by non-covalent interactions, and are thus dependent on proper tertiary structure of the individual peptides. Expression of a recombinant protein in biologically active form, exhibiting the proper tertiary and quaternary structure, by host cells which do not normally express a native form of the protein, frequently presents a significant challenge. Of particular interest in recombinant protein technology is expression of proteins that are membrane-bound in the biologically active form, as soluble proteins. Soluble proteins are useful as therapeutic agents, and in other applications requiring large quantities of highly purified proteins.

Soluble forms of transmembrane proteins have been prepared by deleting the transmembrane and intracytoplasmic domains, and adding an appropriate signal peptide to enable secretion of the soluble form of the protein (Smith et al., *Science* 238:1704, 1987; Treiger et al., *J. Immunol.* 136:4099, 1986). Some soluble proteins have been expressed as fusion proteins in which the extracellular domain of the membrane protein is joined to an immunoglobulin heavy chain constant region (Fanslow et al., *J. Immunol.* 149:65, 1992; Noelle et al., *Proc. Natl. Acad. Sci. U.S.A.* 89:6550, 1992), or with the extracellular domain of the murine T lymphocyte antigen CD8 (Hollenbaugh et al., *EMBO J.* 11:4313, 1992). However, such soluble proteins may not be biologically active due to improper tertiary and/or quaternary structure. Some soluble forms of transmembrane proteins may be biologically active, but poorly expressed, or unstable under the conditions of expression or purification, due to changes in structure as a result of deletion of a portion or portions of the protein.

Leucine zipper is a term that is used to refer to a repetitive heptad motif containing four to five leucine residues present as a conserved domain in several proteins. Leucine zippers fold as short, parallel coiled coils, and are believed to be responsible for oligomerization of the proteins of which they form a domain. Sequences derived from the fos and jun leucine zippers have been used in the formation of bispecific antibodies by expression of DNA encoding the $V_L$ and $V_H$ regions of antibodies as fusion proteins with the leucine zipper sequences. (Kostelny et al., *J. Immunol* 148:1547, 1992) Leucine zipper sequences have also been used to replace the dimerization domain of λ repressor, a soluble DNA-binding protein of bacteriophage λ (Hu et al., *Science* 250:1400, 1990), and in the preparation of a dimeric form of MalE, a maltose binding protein of *E. coli* that is exported into the periplasmic space (Blondel and Bedoulle, *Protein Engineering* 4:457, 1991). Sequences containing the repetitive heptad motif but which vary in the numbers of leucine residues have also been identified. Such sequences also fold as short, parallel coiled coils, and form oligomers in a manner similar to leucine zippers. The term 'zipper domain' is used to refer generally to oligomer-forming peptides that consist of heptad repeats and fold as short, parallel coiled coils.

There is a need in the art to develop methods of expressing biologically active, recombinant, oligomeric proteins, particularly soluble proteins that are membrane-bound in their biologically active configuration.

SUMMARY OF THE INVENTION

The present invention relates to a method of preparing a soluble, oligomeric mammalian protein by culturing a host cell transformed or transfected with an expression vector encoding a fusion protein comprising a zipper domain and a heterologous mammalian protein. In one embodiment, the heterologous mammalian protein comprises an extracellular domain of a mammalian transmembrane protein; the resulting fusion protein forms an oligomer. In another embodiment, the heterologous mammalian protein comprises a soluble protein such as a cytokine; the resulting fusion protein forms an oligomer. In another embodiment, the zipper domain is removed from the fusion protein, by cleavage with a specific proteolytic enzyme. In another embodiment, a hetero-oligomeric protein is prepared by utlizing zipper domains that preferentially form hetero-oligomers.

DETAILED DESCRIPTION OF THE INVENTION

Figure 1B:
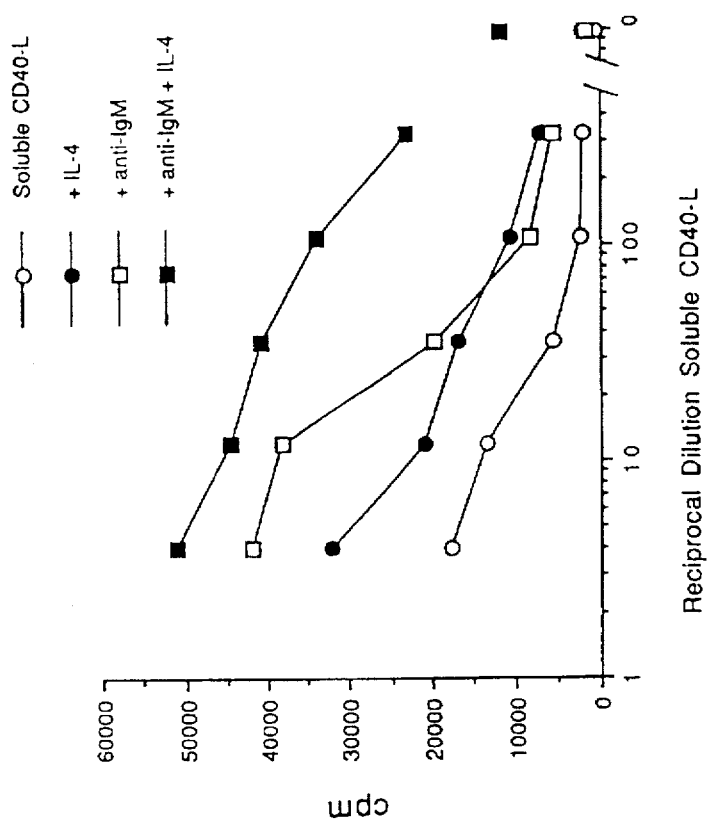
FIG. 1B illustrates the ability of soluble, oligomeric human CD40-L comprising a zipper domain to stimulate the proliferation of human peripheral blood B cells.

The present invention relates to a method of preparing a soluble mammalian protein by culturing a host cell transformed or transfected with an expression vector encoding a fusion protein comprising a zipper domain and a heterologous mammalian protein. In one embodiment, the heterologous mammalian protein comprises an extracellular domain of a mammalian transmembrane protein. Exemplary mammalian transmembrane proteins include members of the tumor necrosis factor/nerve growth factor receptor (TNFR/NGFR) family (Farrah and Smith, *Nature* 358:26, 1992; Goodwin et al., *Cell* 73:447; 1993), which includes CD40 Ligand (CD40-L), CD27 Ligand (CD27-L), OX40 Ligand (OX40-L), and TNF. Structural studies of certain members of this family of proteins indicate that they form homotrimers. The inventive method will also be useful for other members of this family.

Additionally, many other mammalian transmembrane proteins form oligomers, either hetero-oligomers or homo-oligomers, in their biologically-active form. Members of the hematopoietin receptor family (Cosman et al., *Trends Biochem. Sci.* 15:265; 1990) are exemplary of such proteins. Gearing et al. (*Science* 255: 1434, 1992) reported the cloning of a gene encoding a protein (gp130) that conferred high-affinity binding to both leukemia-inhibitory factor (LIF) and Oncostatin M (OSM) when expressed in cells along with a low-affinity LIF receptor. Similar interactions of a low-affinity receptor and a second subunit protein, resulting in a high-affinity receptor have also been proposed for other members of this family (Hayashida et al., *Proc. Natl. Acad. Sci. U.S.A.* 87:0655, 1990; Kitamura et al., *Cell* 66:1165, 1991; Tavernier et al., *Cell* 66:1175, 1991; Devos et al., *EMBO J.* 10:2133, 1991). Soluble forms of the members of the hematopoietin receptor family will exhibit higher affinity for their cognate ligand when expressed as hetero-oliogmers, or in some cases, as homo-oligomers. The same will be true for other transmembrane proteins that comprise two or more subunits.

In another embodiment, the heterologous mammalian protein comprises a soluble protein such as a cytokine; the resulting fusion protein forms an oligomer. Cytokines are soluble mediators released by cells during an immune or inflammatory response, which provide antigenically non-specific, intracellular signals that are crucial in regulating physiological processes. TNF α, TNF β and certain neurotrophins such as nerve growth factor (NGF) belong to the TNF/NGF family. Modeling studies of certain members of this family indicate that they are likely to form oligomers (Goh and Porter, *Protein Eng.* 4:385, 1991; Peitsch and Jongeneel, *Int. Immunol.* 5:233, 1993). Furthermore, other cytokines, including macrophage colony stimulating factor (M-CSF; Pandit et al., *Science* 258:1358, 1992) are also known to be oligomeric. Such cytokines will also be useful in the inventive method, wherein a zipper domain stabilizes the proper quaternary structure of the oligomeric cytokine.

In another embodiment, hetero-oligomeric forms of cytokines are prepared. A fusion protein of granulocyte-macrophage colony stimulating factor (GM-CSF) and Interleukin-3 (IL-3) has been shown to be a more potent proliferation stimulus than either factor alone or IL-3 and GM-CSF combined (U.S. Pat. Nos. 5,073,627 and 5,108,910). Fusion proteins comprising GM-CSF and IL-3 and DNA sequences encoding such fusion proteins are described in U.S. Pat. Nos. 5,073,627 and 5,108,910, respectively, both of which are incorporated by reference herein. A similar, bivalent protein composed of GM-CSF and IL3 may be formed by the expression of these cytokines as fusion proteins comprising zipper domains that preferentially form heterodimers.

In another embodiment, the zipper domain is removed from the fusion protein, for example by cleavage with a specific proteolytic enzyme. In addition to a zipper sequence and a heterologous protein, such fusion proteins also comprise an amino acid sequence recognized, and cleaved, by a selected proteolytic enzyme. The zipper domain functions to stabilize the recombinant fusion protein during expression and secretion. After purification of the secreted protein, the zipper is enzymatically removed by treating with the proteolytic enzyme. The heterologous protein may then become monomeric. Such monomeric forms of soluble proteins will be useful as receptor antagonists, for example, by binding to a cognate receptor and preventing signaling by preventing cross-linking of the receptor.

Zipper Domains

Leucine zippers were originally identified in several DNA-binding proteins (Landschulz et al., *Science* 240:1759, 1988). Zipper domain is a term used to refer to a conserved peptide domain present in these (and other) proteins, which is responsible for oligomerization of the proteins. The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240: 1759, 1988). The products of the nuclear oncogenes fos and jun comprise zipper domains preferentially form a heterodimer (O'Shea et al., *Science* 245:646, 1989; Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547,1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been recently reported to play a role in oligomerization of heat-shock transcription factors (Rabindran et al., *Science* 259:230, 1993).

Zipper domains fold as short, parallel coiled coils. (O'Shea et al., *Science* 254:539; 1991) The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated (abcdefg)$_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek et al., *Int. J. Peptide Res.* 38:229, 1991). Lovejoy et al. recently reported the synthesis of a triple-stranded α-helical bundle in which the helices run up-up-down (*Science* 259:1288, 1993). Their studies confirmed that hydrophobic stabilization energy provides the main driving force for the formation of coiled coils from helical monomers. These studies also indicate that electrostatic interactions contribute to the stoichiometry and geometry of coiled coils.

Several studies have indicated that conservative amino acids may be substituted for individual leucine residues with minimal decrease in the ability to dimerize; multiple changes, however, usually result in loss of this ability (Landschulz et al., *Science* 243:1681, 1989; Turner and Tjian, *Science* 243:1689, 1989; Hu et al., *Science* 250:1400, 1990). van Heekeren et al. reported that a number of different amino residues can be substituted for the leucine residues in the zipper domain of GCN4, and further found that some GCN4 proteins containing two leucine substitutions were weakly active (*Nucl. Acids Res.* 20:3721, 1992). Mutation of the first and second heptadic leucines of the zipper domain of the measles virus fusion protein (MVF) did not affect syncytium formation (a measure of virally-induced cell fusion); however, mutation of all four leucine residues prevented fusion completely (Buckland et al., *J. Gen. Virol.* 73:1703, 1992). None of the mutations affected the ability of MVF to form a tetramer.

Recently, amino acid substitutions in the a and d residues of a synthetic peptide representing the GCN4 zipper domain have been found to change the oligomerization properties of the zipper domain (Alber, Sixth Symposium of the Protein Society, San Diego, Calif.). When all residues at position a are changed to isoleucine, the zipper still forms a parallel dimer. When, in addition to this change, all leucine residues at position d are also changed to isoleucine, the resultant peptide spontaneously forms a trimeric parallel coiled coil in solution. Substituting all amino acids at position d with isoleucine and at position a with leucine results in a peptide that tetramerizes. Peptides containing these substitutions are still referred to as zipper domains since the mechanism of oligomer formation is believed to be the same as that for traditional leucine zipper domains such as those described above. However, prior to the present invention, the effect of these substitutions upon longer peptides of which the zipper is but a small domain was not known, nor was it known if peptides comprising these sequences could be expressed and secreted by cells.

Preparation of Gene Fragments and Oligonucleotides

Oligonucleotide fragments of about 12 to about 20 nucleotides may be prepared according to methods that are known in the art, for example, by using an automated DNA synthesizer. Several such fragments may be synthesized, which encode overlapping portions of a peptide, for example, a zipper domain. Due to the degeneracy of the genetic code, most amino acids are encoded by two or more different nucleotide triplets. The selection of a triplet to encode a given amino acid will depend upon the organism in which the final gene product is to be expressed, among other considerations. Overlapping fragments may then be joined to form a DNA encoding a peptide of interest.

A polymerase chain reaction (PCR) technique (Saiki et al., *Science* 239:487, 1988) may be employed to amplify gene fragments encoding all or a portion of a protein of interest, using 5' (upstream) and 3' (downstream) oligonucleotide primers derived from the known DNA sequence of the gene, or a gene encoding a related protein. An exemplary set of PCR conditions includes: one cycle at 94° C. for 2 minutes, followed by 42° C. for two minutes; 30 cycles at 72° C. for 1.5 minutes, followed by 94° C. for one minute, then 48° C. for 1 minute; and one cycle at 72° C. for seven minutes. Restriction enzyme sites can also be added to the DNA sequences of interest, in order to facilitate ligation of the resulting PCR product with a plasmid or vector, or with an additional DNA sequence or sequences. Amplified DNA sequences may be joined substantially as described by Yon and Fried (*Nucleic Acids Res.* 17:4895; 1989).

For example, as disclosed in U.S. Ser. No. 08/097,827, filed Jul. 23, 1993, now allowed, the disclosure of which is incorporated by reference herein, full length mouse OX40 was cloned using 5' (upstream) and 3' (downstream) oligonucleotide primers based on the published sequence of rat OX40. The upstream primer comprised a recognition site for the restriction endonuclease Spe I upstream of a sequence encoding the first six (N-terminal) amino acids of rat OX40. The downstream primer comprised a recognition site for the restriction endonuclease Spe I upstream of a sequence encoding the last five (C-terminal) amino acids of full-length OX40. The PCR product was digested with Spe I, and an approximately 800 bp fragment was isolated by gel filtration, and used in a second round of PCR reaction. The isolated fragment was ligated into Spe I cut plasmid, pBLUESCRIPT SK® (Stratagene Cloning Systems, La Jolla, Calif.), which had been treated with calf intestine alkaline phosphatase (CIAP) to prevent self-ligation.

In another example, a DNA encoding only the extracellular region of a transmembrane protein can be obtained by deleting DNA encoding the intracellular and transmembrane portions of the transmembrane protein. Methods to determine which residues should be deleted and for performing the actual deletions are well known in the art. For example, Smith et al. describe a soluble form of the human CD4 antigen prepared by deleting the transmembrane and intracellular portions of the CD4 antigen (*Science* 238:1704, 1987). Treiger et al. prepared a soluble form of an Interleukin-2 receptor using similar methods using similar methods (*J. Immunol.* 136:4099, 1986).

A fusion protein may be formed from an extracellular region and a protein (or portion thereof) that is known to be secreted. For example, soluble proteins comprising an extracellular domain from a membrane-bound protein and an immunoglobulin heavy chain constant region was described by Fanslow et al., *J. Immunol.* 149:65, 1992 and by Noelle et al., *Proc. Natl. Acad. Sci. U.S.A.* 89:6550, 1992. The extracellular domain of the murine T lymphocyte antigen CD8 has also be utilized to form soluble fusion proteins (Hollenbaugh et al., *EMBO J.* 11:4313, 1992).

Preparation of Fusion Proteins

Fusion proteins are polypeptides that comprise two or more regions derived from different, or heterologous, proteins or peptides. Fusion proteins are prepared using conventional techniques of enzyme cutting and ligation of fragments from desired sequences. PCR techniques employing synthetic oligonucleotides may be used to prepare and/or amplify the desired fragments. Overlapping synthetic oligonucleotides representing the desired sequences can also be used to prepare DNA constructs encoding fusion proteins. Fusion proteins can comprise several sequences, including a leader (or signal peptide) sequence, linker sequence, a zipper sequence, or other oligomer-forming sequences, and sequences encoding highly antigenic moieties that provide a means for facile purification or rapid detection of a fusion protein.

Signal peptides facilitate secretion of proteins from cells. An exemplary signal peptide is the amino terminal 25 amino acids of the leader sequence of murine interleukin-7 (IL-7; Namen et al., *Nature* 333:571; 1988). Other signal peptides may also be employed furthermore, certain nucleotides in the IL-7 leader sequence can be altered without altering the amino acid sequence. Additionally, amino acid changes that do not affect the ability of the IL-7 sequence to act as a leader sequence can be made. The Flag® octapeptide (SEQ ID NO:1; Hopp et al., *Bio/Technology* 6:1204, 1988) does not alter the biological activity of fusion proteins, is highly antigenic and provides an epitome reversibly bound by a specific monoclonal antibody, enabling rapid detection and facile purification of the expressed fusion protein. The Flag® sequence is also specifically cleaved by bovine mucosal enterokinase at the residue immediately following the Asp-Lys pairing. Fusion proteins capped with this peptide may also be resistant to intracellular degradation in *E. coli*. A murine monoclonal antibody that binds the Flag® sequence has been deposited with the ATCC under accession number HB 9259; methods of using the antibody in purification of fusion proteins comprising the Flag® sequence are described in U.S. Pat. No. 5,011,912, which is incorporated by reference herein.

A protein of interest may be linked directly to another protein to form a fusion protein; alternatively, the proteins may be separated by a distance sufficient to ensure that the proteins form proper secondary and tertiary structures. Suitable linker sequences (1) will adopt a flexible extended conformation, (2) will not exhibit a propensity for developing an ordered secondary structure which could interact with the functional domains of fusion proteins, and (3) will have minimal hydrophobic or charged character which could promote interaction with the functional protein domains. Typical surface amino acids in flexible protein regions include Gly, Asn and Ser. Virtually any permutation of amino acid sequences containing Gly, Ash and Ser would be expected to satisfy the above criteria for a linker sequence. Other near neutral amino acids, such as Thr and Ala, may also be used in the linker sequence. The length of the linker sequence may vary without significantly affecting the biological activity of the fusion protein. Linker sequences are unnecessary where the proteins being fused have non-essential N- or C-terminal amino acid regions which can be used to separate the functional domains and prevent steric interference. Exemplary linker sequences are described in U.S. Pat. Nos. 5,073,627 and 5,108,910, the disclosures of which are incorporated by reference herein.

When an oligomeric fusion protein is formed from the extracellular portion of a transmembrane protein, a DNA sequence encoding an oligomer-forming domain, such as a zipper domain, is fused to a DNA sequence encoding the extracellular region of the transmembrane protein. The members of the fusion protein are joined such that the oligomer-forming domain of the fusion protein is located in the same orientation relative to the fusion protein as the transmembrane and intracytoplasmic reigns of the native transmembrane protein. An oligomeric fusion protein will be stabilized by the coiled-coil interaction of zipper domain. Thus, in one example, a fusion protein comprising an extracellular region derived from a ligand for CD40 (CD40-L), a type II transmembrane protein described in U.S. Ser. No. 08/249,189, filed May 24, 1994, now pending, a continuation-in-part of U.S. Ser. No. 07/969,703, now abandoned, the disclosure of which is incorporated by reference herein, the oligomer-forming domain, a zipper sequence, is fused to the amino-proximal end of the extracellular region. In a fusion protein derived from a type I transmembrane protein, the oligomer-forming domain would be fused to the carboxy-proximal end of the extracellular region of the type I transmembrane protein. Other transmembrane proteins traverse the cell membrane more than once. Such transmembrane proteins will have two or more different extracellular regions. Soluble, oligomeric fusion proteins may also be prepared from two or more of such different extracellular regions from the same transmembrane protein.

Oligomeric forms of proteins that occur naturally in soluble form may also be prepared. In such cases, the oligomer-forming domain is joined to the soluble protein such that formation of an oligomer follows the conformation of the biologically active, soluble protein. Furthermore, either homo-oligomeric proteins or hetero-oligomeric proteins can be prepared, depending upon the whether the oligomerizing domain(s) of the fusion protein preferentially form hetero-ologimers or homo-oligomers.

Expression Vectors

Recombinant expression vectors for expression of a fusion protein comprising an oligomer-forming domain and a heterologous mammalian protein by recombinant DNA techniques include a DNA sequence comprising a synthetic or cDNA-derived DNA fragment encoding an oligomer-forming domain, linked in frame to a DNA fragment encoding the heterologous protein. These DNA fragments are operably linked to suitable transcription and/or translational regulatory nucleotide sequences, such as those derived from a mammalian, microbial, viral, or insect gene. Examples of regulatory sequences include sequences having a regulatory role in gene expression (e.g., a transcription promoter or enhancer), an operator sequence to control transcription, a sequence encoding an mRNA ribosomal binding site, a polyadenylation site, splice donor and acceptor sites, and appropriate sequences which control transcription, translation initiation and termination. In addition, sequences encoding signal peptides can be incorporated into expression vectors. For example, a DNA sequence for a signal peptide (secretory leader) may be operably linked to a DNA encoding a fusion protein comprising an oligomer-forming domain and a heterologous mammalian protein. The signal peptide is expressed as a part of a precursor amino acid sequence; the signal peptide enables improved extracellular secretion of translated fusion polypeptide by a yeast host cell.

Nucleotide sequences are operably linked when the regulatory sequence functionally relates to the DNA encoding the fusion protein. Thus, a promoter nucleotide sequence is operably linked to a DNA encoding a fusion protein if the promoter nucleotide sequence controls the transcription of the DNA encoding the fusion protein. Still further, a ribosome binding site may be operably linked to a sequence for a fusion protein if the ribosome binding site is positioned within the vector to encourage translation.

Transcription and translational control sequences for mammalian host cell expression vectors may be excised from viral genomes. For example, commonly used mammalian cell promoter sequences and enhancer sequences are derived from Polyoma virus, Adenovirus 2, Simian Virus 40 (SV40), and human cytomegalovirus. DNA sequences derived from the SV40 viral genome, for example, the SV40 origin, early and late promoters, enhancer, splice, and polyadenylation sites may be used to provide the other genetic elements required for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary mammalian expression vectors can be constructed as disclosed by Okayama and Berg (*Mol. Cell. Biol.* 3:280, 1983). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. For expression of a type II protein extracellular region, such as OX40-L, a heterologous signal sequence may be added, such as the signal sequence for interleukin-7 (IL-7) described in U.S. Pat. No. 4,965,195, or the signal sequence for interleukin-2 receptor described in U.S. patent application Ser. No. 06/626,667 filed on Jul. 2, 1984. Another exemplary vector is pDC406, which includes regulatory sequences derived from SV40, human immunodeficiency virus (HIV), and Epstein-Bart virus (EBV).

Expression vectors transfected into prokaryotic host cells generally comprise one or more phenotypic selectable markers. A phenotypic selectable marker is, for example, a gene encoding a protein that confers antibiotic resistance or that supplies an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and a OX40-L DNA sequence. Other commercially vectors include, for example, pKK223-3 (Pharmacia Fine Chemicals, Uppsala, Sweden) and pGEM1 (Promega Biotec, Madison, Wis., USA).

Promoter sequences are commonly used for recombinant prokaryotic host cell expression vectors. Common promoter sequences include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857Its thermolabile repressor sequence. Plasmid vectors available from the American Type Culture Collection which incorporate derivatives of the λ $P_L$ promoter include plasmid pHUB2 (resident in *E. coil* strain JMB9 (ATCC 37092)) and pPLc28 (resident in *E. coli* RR1 (ATCC 53082)).

Host Cells

Suitable host cells for expression of a fusion protein comprising an oligomer-forming domain and a heterologous mammalian protein include prokaryotes and yeast or higher eukaryotic cells. Prokaryotes include gram negative or gram positive organisms, for example, *E. coli* or Bacilli. Suitable prokaryotic host cells for transformation include, for example, *E. coli*, *Bacillus subtilis*, *Salmonella typhimurium*, and various other species within the genera Pseudomonas, Streptomyces, and Staphylococcus. Higher eukaryotic cells include established cell lines of mammalian origin. Cell-free translation systems could also be employed to produce a fusion protein comprising an oligomer-forming domain and a heterologous mammalian protein using an RNA derived from DNA constructs disclosed herein.

In a prokaryotic host cell, such as *E. coli*, a fusion protein may include an N-terminal methionine residue to facilitate expression of the recombinant polypeptide in the prokaryotic host cell. The N-terminal Met may be cleaved from the expressed recombinant fusion protein. Prokaryotic host cells may be used for expression of fusion proteins that do not require extensive proteolytic or disulfide processing.

Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). An expression vector carrying the recombinant fusion protein DNA is transfected or transformed into a substantially homogeneous culture of a suitable host microorganism or mammalian cell line according to methods that are known in the art, to form transfected or transformed host cells that express the fusion protein. Expressed fusion protein will be located within the host cell and/or secreted into culture supernatant fluid, depending upon the nature of the host cell and the gene construct inserted into the host cell.

A fusion protein comprising an oligomer-forming domain and a heterologous mammalian protein may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657.

Yeast vectors can be assembled, for example, using DNA sequences from pBR322 for selection and replication in *E. coli* (Amp$^r$ gene and origin of replication). Other yeast DNA sequences that can be included in a yeast expression construct include a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader sequence directs secretion of heterologous polypeptides. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. For example, one can select for Trp$^+$ transformants in a selective medium, wherein the selective medium consists of 0.67% yeast nitrogen base, 0.5% casamino acids, 2% glucose, 10 μg/ml adenine and 20 μg/ml uracil. Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant fusion protein. Examples of suitable mammalian host cell lines include the COS-7 line of monkey kidney cells (ATCC CRL 1651; Gluzman et al., *Cell* 23:175, 1981), L cells, C127 cells, 3T3 cells (ATCC CRL 163), Chinese hamster ovary (CHO) cells, HeLa cells, BHK (ATCC CRL 10) cell lines, and CV-1/EBNA cells (ATCC CRL 10478). The CV-1/EBNA cell line was derived by transfection of the CV-1 cell line with a gene encoding Epstein-Barr virus nuclear antigen-1 (EBNA-1) and constitutively express EBNA- 1 driven from human CMV immediate-early enhancer/promoter. An EBNA-1 gene allows for episomal replication of expression vectors that contain the EBV origin of replication.

Protein Purification

Purified soluble fusion proteins are prepared by culturing suitable host/vector systems to express the recombinant soluble fusion proteins, which are then purified from culture media or cell extracts, using standard methods of protein purification that are optimized for each individual soluble fusion protein.

For example, supernatants from systems which secrete recombinant protein into culture media are clarified, and concentrated using a commercially available protein concentration filter, for example, an Amicon or Millipore Pellicon ultrafiltration unit. Following the concentration step, the concentrate can be applied to a suitable purification matrix. Suitable matrices include those useful in affinity chromatography. For example, a suitable affinity matrix can comprise a cognate protein to which the fusion proteins binds, or lectin or antibody molecule which binds the fusion protein, bound to a suitable support.

Alternatively, an ion exchange resin can be employed, for example, an anion exchange resin comprising a matrix or substrate having pendant diethylaminoethyl (DEAE) groups, or other suitable anion exchangers. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups.

One or more reversed-phase high performance liquid chromatography (RP-HPLC) steps employing hydrophobic RP-HPLC media, e.g., silica gel having pendant methyl or other aliphatic groups, can be employed to further purify a soluble fusion protein. Size exclusion chromatography will also be useful in purifying soluble fusion proteins. Additionally, hydrophobic supports can also be used under low pressure conditions; an exemplary medium is phenyl-sepharose. Some or all of the foregoing purification steps, in various combinations, can also be employed to provide a homogeneous recombinant protein.

Biological Activity

Biological activity of recombinant, soluble fusion proteins is mediated by binding of the recombinant, soluble fusion protein to a cognate molecule. A cognate molecule is defined as a molecule which binds the recombinant soluble fusion protein in a non-covalent interaction based upon the proper conformation of the recombinant soluble fusion protein and the cognate molecule. For example, for a recombinant soluble fusion protein comprising an extracellular region of a receptor, the cognate molecule comprises a ligand which binds the extracellular region of the receptor. Conversely, for a recombinant soluble fusion protein comprising a ligand, the cognate molecule comprises a receptor (or binding protein) which binds the ligand.

Binding of a recombinant fusion protein to a cognate molecule is a marker for biological activity. Such binding activity may be determined, for example, by competition for binding to the binding domain of the cognate molecule (i.e. competitive binding assays). One configuration of a competitive binding assay for a recombinant soluble fusion protein comprising a ligand uses a radiolabeled, soluble receptor, and intact cells expressing a native form of the ligand. Such an assay is illustrated in Example 4 herein. Similarly, a competitive assay for a recombinant soluble fusion protein comprising a receptor uses a radiolabeled, soluble ligand, and intact cells expressing a native form of the receptor. Instead of intact cells expressing a native form of the cognate molecule, one could substitute purified cognate molecule bound to a solid phase. Competitive binding assays can be performed using standard methodology. Qualitative or semi-quantitative results can be obtained by competitive autoradiographic plate binding assays, or fluorescence activated cell sorting, or Scatchard plots may be utilized to generate quantitative results.

Biological activity may also be measured using bioassays that are known in the art, such as a cell proliferation assay. Exemplary bioassays are described in Example 2 herein. The type of cell proliferation assay used will depend upon the recombinant soluble fusion protein. A bioassay for a recombinant soluble fusion protein that in its native form acts upon T cells will utilize purified T cells obtained by methods that are known in the art. Such bioassays include costimulation assays in which the purified T cells are incubated in the presence of the recombinant soluble fusion protein and a suboptimal level of a mitogen such as Con A or PHA. Similarly, purified B cells will be used for a recombinant soluble fusion protein that in its native form acts upon B cells. Other types of cells may also be selected based upon the cell type upon which the native form of the recombinant soluble fusion protein acts. Proliferation is determined by measuring the incorporation of a radiolabeled substance, such as $^3H$ thymidine, according to standard methods.

Yet another type assay for determining biological activity is induction of secretion of secondary molecules. For example, certain proteins induce secretion of cytokines by T cells. T cells are purified and stimulated with a recombinant soluble fusion protein under the conditions required to induce cytokine secretion (for example, in the presence of a comitogen). Induction of cytokine secretion is determined by bioassay, measuring the proliferation of a cytokine dependent cell line. Similarly, induction of immunoglobulin secretion is determined by measuring the amount of immunoglobulin secreted by purified B cells stimulated with a recombinant soluble fusion protein that acts on B cells in its native form, using a quantitative (or semi-quantitative) assay such as an enzyme immunoassay. Example 2 presents such assays.

The relevant disclosures of all references cited herein are specifically incorporated by reference. The following examples are offered by way of illustration, and not by way of limitation.

Example 1

This example describes construction of a CD40-L DNA construct to express a soluble CD40-L fusion protein referred to as trimeric CD40-L. CD40-L is a type II transmembrane protein found on activated T cells, that acts as a ligand for the B cell antigen, CD40 (Armitage et al., *Nature* 357:80, 1992; Spriggs et al., *J. Exp. Med.* 176:1543, 1992). A gene encoding CD40-L has been cloned and sequenced as described in U.S. Ser. No. 08/249,189, filed May 24, 1994, now pending, a continuation-in-part of U.S. Ser. No. 07/969, 703, filed Oct. 23, 1992, now abandoned, the disclosure of which is incorporated by reference herein. CD40-L is a member of the Tumor Necrosis Factor (TNF) family of proteins; several members of this family are believed to exist in trimeric form.

Trimeric CD40-L contains a leader sequence, a 33 amino acid sequence referred to as a "zipper" (SEQ ID NO:2), and an eight amino acid hydrophilic sequence described by Hopp et al. (Hopp et al., Bio/Technology 6:1204, 1988; SEQ ID NO:1; referred to as Flag®), followed by the extracellular region of human CD40-L (amino acid 50 to amino acid 261 of SEQ ID NOs:3 and 4). The utility of the leader and the Flag® sequences have been described in previously. The 33 amino acid sequence presented in SEQ ID NO:2 trimerizes spontaneously in solution. Fusion proteins comprising this 33 amino acid sequence are thus expected to form trimers or multimers spontaneously.

The construct is prepared by synthesizing oligonucleotides representing a leader sequence, the 33 amino acid sequence described above (SEQ ID NO:2), and the Flag® sequence (SEQ ID NO:1), then ligating the final product to a DNA fragment encoding the extracellular region of human CD40-L (amino acids 50 to 261 of SEQ ID NOs:3 and 4).

The resulting ligation product in expression vector pDC406 was transfected into the monkey kidney cell line CV-1/EBNA (ATCC CRL 10478). The pDC406 plasmid includes regulatory sequences derived from SV40, human immunodeficiency virus (HIV), and Epstein-Barr virus (EBV). The CV-1/EBNA cell line was derived by transfection of the CV-1 cell line with a gene encoding Epstein-Barr virus nuclear antigen-1 (EBNA-1) that constitutively expresses EBNA-1 driven from the human CMV intermediate-early enhancer/promoter. The EBNA-1 gene allows for episomal replication of expression vectors, such as pDC406, that contain the EBV origin of replication.

Once cells expressing the fusion construct are identified, large scale cultures of transfected cells are grown to accumulate supernatant from cells expressing soluble, oligomeric CD40-L. The soluble, oligomeric CD40-L fusion protein in supernatant fluid is purified by affinity purification substantially as described in U.S. Pat. No. 5,011,912. sCD40-L may also be purified using other protein purification methods, as described herein. Silver-stained SDS gels of the soluble, oligomeric CD40-L fusion protein can be prepared to determine purity. Similar methods are used to prepare and purify a trimer-forming construct comprising the extracellular region of murine CD40-L (amino acid 50 to amino acid 260 of SEQ ID NOs:5 and 6). Soluble CD40-L exhibits similar biological activity to that of membrane-bound CD40-L, as shown in Example 2.

Example 2

This example illustrates B cell proliferative activity and induction of polyclonal immunoglobulin secretion using soluble, oligomeric CD40-L prepared as described in Example 1. Human B cells were purified substantially as described in Armitage et al. (J. Immunol. 150:3671; 1993). Briefly, tonsillar tissue was gently teased and the resulting cell suspension centrifuged over Histopaque® (Sigma, St. Louis, Mo.). T cell-depleted preparations of cells ($E^{31}$) were obtained by removing T cells by rosetting with 2-aminoethylisothiouronium bromide-treated SRBC (sheep red blood cells) and treatment with B cell Lympho-kwik (One Lambda Inc., Los Angeles, Calif.) for 1 hour at 37° C. to lyse contaminating non-B cells. Peripheral blood mononuclear cells (PBMC) were isolated in the same manner, with the additional step of treating the partially purified cells with 5 mM leucine methyl ester (Leu ME; Sigma, St. Louis, Mo.) in serum-free medium for one hour at room temperature prior to the Lympho-kwik step, to remove phagocytic cells.

Figure 1A:
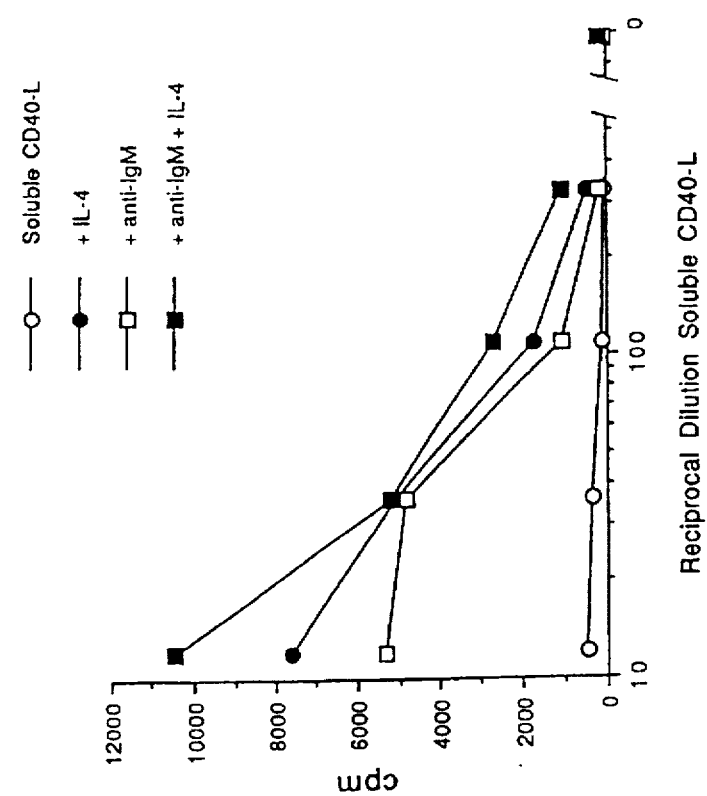
FIG. 1A illustrates the ability of soluble, oligomeric human CD40-L comprising a zipper domain to stimulate the proliferation of human tonsillar B cells.

B cell proliferation was measured with a $^3$H-thymidine incorporation assay, substantially as described in Armitage et al., supra. Cells were cultured for three days in the presence of soluble, oligomeric CD40-L (sCD40-L), alone or in the presence of 5 ng/ml IL-4 (Immunex Corporation, Seattle, Wash.), 5 µg/ml anti-IgM coated beads (BioRad, Richmond, Calif.), or a combination of IL-4 and anti-IgM. The results of a representative experiment to evaluate the ability of sCD40-L to induce B cell proliferation are shown in FIGS. 1A and 1B. sCD40-L induced proliferation of tonsillar B cells in the presence of IL-4, anti-IgM, or a combination of these to co-factors (FIG. 1A). sCD40-L also induced proliferation of peripheral blood B cells in the presence of IL-4, anti-IgM, or a combination of these to co-factors, and with B cells obtained from some donors, a moderate level of proliferation in the absence of any co-factor (FIG. 1B). These results parallel the results obtained with recombinant, membrane-bound CD40-L described in Armitage et al. supra.

Polyclonal immunoglobulin secretion was determined by isotype-specific ELISA on supernatant fluid from 10 day cultures of 1×10$^5$ B cells per well, substantially as described in Armitage et al., supra. Purified B cells were stimulated with a 1:20 dilution of supernatant fluid containing soluble, oligomeric CD40-L (sCD40-L), a 1:20 dilution of control supernatant (control S/N; conditioned medium from cells transfected with vector alone), or transfected CV-1/EBNA cells expressing membrane-bound CD40-L (CV1/CD40L; 3×10$^4$ cells/well), in the presence or absence of 10 ng/ml of either IL-2, IL-4 (both from Immunex Corporation, Seattle, Wash.) or IL-10 (Genzyme Corporation, Boston, Mass.). The results of a representative experiment measuring immunoglobulin secretion are presented in Table 1; values given represent the quantity of each isotype secreted by the induced B cells in ng/ml, as measured by ELISA.

TABLE 1

Immunoglobulin Secretion Induced by CD40 Ligand

| | Medium alone | Medium + IL-2 | Medium + IL-4 | Medium + IL-10 | Isotype |
|---|---|---|---|---|---|
| Control S/N | 114.9 | 424.5 | 69.4 | 132.2 | IgM |
| sCD40-L | 212.3 | 2827.5 | 51.5 | 1726.5 | |
| CV1/CD40L | 91.8 | 1965.0 | 97.4 | 574.1 | |
| Control S/N | 16.2 | 161.0 | 40.1 | 22.7 | IgG$_1$ |
| sCD40L-3 | 25.8 | 933.2 | 122.3 | 231.9 | |
| CV1/CD40L | 2.3 | 428.0 | 27.9 | 247.0 | |
| Control S/N | 45.1 | 44.2 | 39.6 | 50.0 | IgA |
| sCD40L-3 | 56.7 | 248.0 | 48.7 | 353.9 | |
| CV1/CD40L | 64.7 | 513.8 | 34.7 | 447.2 | |
| Control S/N | <0.3 | <0.3 | <0.3 | <0.3 | IgE |
| sCD40L-3 | <0.3 | <0.3 | 67.0 | <0.3 | |
| CV1/CD40L | <0.3 | <0.3 | 77.6 | <0.3 | |

These results indicated that soluble, oligomeric CD40-L induced polyclonal immunoglobulin secretion in the same manner as membrane-bound CD40-L. IL-2 and IL-10 enhanced secretion of IgM, IgG$_1$ and IgA; secretion of measurable amounts of IgE occurred only in the presence of IL-4, just as observed for membrane-bound CD40-L. The same pattern of immunoglobulin secretion was present when B cells from several different donors were tested, although the absolute quantities varied from donor to donor. In similar experiments in a murine system, a soluble, oligomeric construct of a murine CD40-L also gave comparable results to membrane-bound murine CD40-L.

Example 3

This example describes construction of a CD27-L DNA construct to express a soluble, oligomeric CD27-L fusion protein referred to as sCD27L-3. CD27-L is a type II transmembrane protein that binds to the lymphocyte antigen, CD27. CD27 is found on most peripheral blood T cells (Bigler et al., *J. Immunol.* 141:21, 1988; van Lier et al., *Eur. J. Immunol.* 18:811, 1988), and a subpopulation of B cells (Maurer et al., *Eur. J. Immunol.* 20:2679, 1990). CD27-L is a member of the tumor necrosis factor family of cytokines. A gene encoding CD27-L has been cloned and sequenced as described in Goodwin et al., *Cell* 73:447 (1993), and in U.S. Ser. No. 08/106,507, filed Aug. 13, 1993, now pending, a continuation-in-part of U.S. Ser. No. 07/941,648, filed Sep. 8, 1992, now abandoned, the disclosures of which are incorporated by reference herein.

The construct encoding sCD27L-3 contains a leader sequence, a 37 amino acid sequence comprising a zipper domain, and the extracellular region of human CD27-L from amino acid 39 to amino acid 193; the nucleotide and amino acids sequences are presented in SEQ ID NOs:7 and 8. The construct was prepared by using methods that are well-known in the art to obtain a DNA encoding the extracellular region of CD27-L. Briefly, the extracellular region of CD27-L was amplified from a full-length CD27-L cDNA using a PCR technique. The primers used were derived from the extracellular region of CD27-L (SEQ ID NO:7, nucleotides 222-245, for the 5' primer, and the complement of nucleotides 663-689 for the 3' primer) with addition of sequences encoding desired restriction enzyme sites (ACTAGT, which contains a Spe I site, for the 5' primer, and GCGGCCGC, which contains a Not I site, for the 3' primer). The amplified PCR product, representing the extracellular domain of CD27-L, was cloned into an Spe I/Not I-cut SMAG (pDC206) vector. SMAG vector is a derivative of pDC201 (Sims et al., *Science* 241:585, 1988) that contains the murine IL-7 leader sequence. The vector was amplified, then cut with Spe I and treated with calf intestinal alkaline phosphatase. Oligonucleotides based on the amino acid sequence of a zipper (SEQ ID NO:1) were synthesized by standard methodology, and ligated with the Spe I-cut vector, to form an expression vector comprising a murine IL-7 leader sequence (Namen et al., *Nature* 333:571; 1988), a zipper domain, and the extracellular domain of CD27-L. The expression vector was referred to as pDC206/sCD27L-3.

pDC206/sCD27L-3 was co-transfected into the monkey kidney cell line CV-1/EBNA (ATCC CRL 10478) along with a pSV3Neo plasmid. pSV3Neo (Mulligan and Berg, *Proc. Natl. Acad. Sci. U.S.A.* 78:2072; 1981) is a plasmid which expresses the SV40 T antigen, and thus allows for the episomal replication of the pDC206 plasmid.

Once cells expressing the fusion construct are identified, large scale cultures of transfected cells are grown to accumulate supernatant from cells expressing the soluble, oligomeric CD27-L fusion protein (referred to as sCD27L-3). sCD27L-3 in supernatant fluid is purified by affinity purification substantially as described in U.S. Pat. No. 5,011,912. sCD27L-3 may also be purified using other protein purification methods, as described herein. Silver-stained SDS gels of the soluble, oligomeric CD27-L fusion protein can be prepared to determine purity. sCD27L-3 binds to soluble CD27, and inhibits binding of soluble CD27 to cells expressing CD27-L, as described in Example 4.

Example 4

This example illustrates a binding inhibition activity of sCD27L-3. A soluble form of the human lymphocyte surface antigen CD27 was prepared substantially as described by Fanslow et al., *J. Immunol.* 149:65 (1992), to form a dimeric, Fc fusion construct referred to as CD27.Fc (Goodwin et al., *Cell* 73:447; 1993). CD27.Fc comprises the extracellular region of CD27 and an Fc region from a human IgG$_1$. sCD27L-3 inhibits binding of CD27.Fc to MP. 1 cell, a human, Epstein-Barr virus-transformed B cell line that expresses endogenous CD27-L.

Conditioned supernatant fluid from CV-1/EBNA cells transfected with pDC206/sCD27L-3 was titrated in a 96 well plate. A constant amount of CD27.Fc (1 μg/well) was added to each well, followed by 1-2×10$^6$ MP.1 cells per well, in binding medium (RPMI-1640 containing 1% bovine serum albumin, 0.2 % sodium azide and 20 mM HEPES, pH 7.2). The plate was incubated at 37° C. for one hour. Cells were washed twice with PBS, then pelleted by centrifugation. $^{125}$I-mouse anti-human IgG Fc was added to each well at a constant concentration, and the plate incubated for an additional hour at 37° C. The $^{125}$I-mouse anti-human IgG Fc bound to the CD27.Fc that bound to the MP.1 cells. After the final incubation, cells were harvested over pthalate oil-containing tubes to separate the bound and free $^{125}$I-mouse anti-human IgG Fc, and the amount of radioactivity quantitated using a gamma counter.

Figure 2:
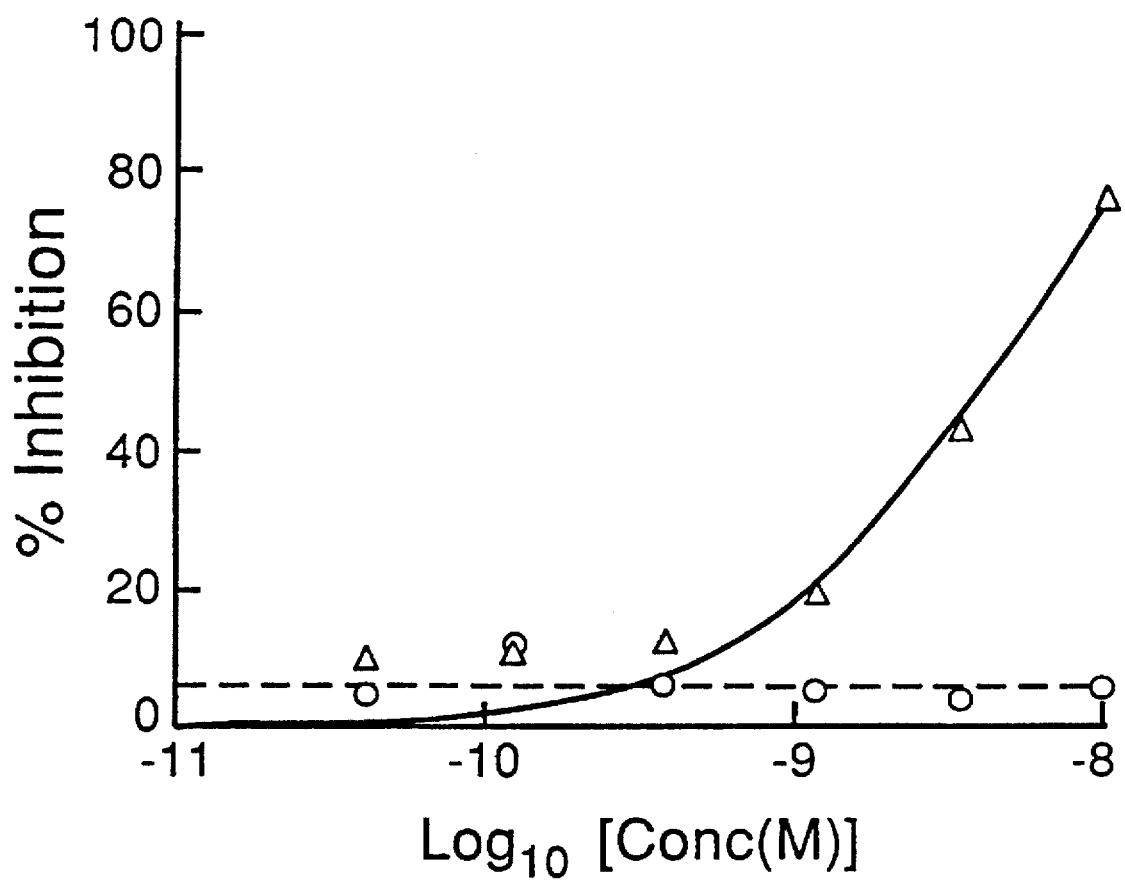
FIG. 2 illustrates the inhibition of binding of CD27.Fc to MP.1 cells, which express CD27-L, by a soluble form of CD27-L, sCD27L-3, that comprises a zipper domain.

The results of this experiment are presented in FIG. 2. sCD27L-3 exhibited a dose-dependent inhibition of the binding of CD27.Fc to MP.1 cells. By comparing the concentration at which the inhibition of binding of CD27.Fc is at 50% to the titration of inhibition by sCD27L-3, it was estimated that the concentration of sCD27L-3 in the conditioned medium was between 18 and 40 μg/ml. In making this comparison, the MW of sCD27L-3 was estimated to be 135 Kd (estimated MW of extracellular region of CD27-L was 45 Kd, multiplied by three for formation of trimer), and the binding of sCD27L-3 to CD27.Fc was assumed to occur at a molar ratio. The K$_i$ was estimated to be 10 times the K$_a$, which was 3×10$^{-7}$M$^{-1}$, and the initial concentration was assumed to be 1×10$^{-8}$M. The results demonstrated that the initial assumption of a concentration of 1×10$^{-8}$M was approximately 10-fold too low, and a 1:3 dilution of the supernatant fluid actually gave an estimated concentration of 1×10$^{-7}$M.

Example 5

This example illustrates preparation of a number of muteins of a CD40 ligand/zipper domain fusion protein. Mutations for constructs to be expressed in yeast (mutants 14, 18, 32, 41, 43, 10PP and 18PP) were generated by PCR misincorporation (Mulrad et al *Yeast* 8:79, 1992), and selected based on an apparent increase in secretion as improved secretion mutants. Mutants 14, 18, 32, 41, and 43 were isolated in *S. cerevisiae*. Mutants 10PP and 18PP were isolated in *P. pastoris*. Mutations for constructs to be expressed in mammalian cells (LZ12.V) were also prepared using PCR, and were the random product of PCR. The types of mutations obtained and their effect on activity (ability to bind CD40) are shown in Table 2 below.

TABLE 2

Mutations present in the CD40 ligand/zipper domain fusion protein

| Mutant No.: | Zipper Domain Mutation[a] | CD40L Domain Mutations[b] | Activity | Type of Mutant |
|---|---|---|---|---|
| 14 | I12N | K260N | + | random mutant |
| 18 | L13P | A130P,R181Q | + | random mutant |
| 32 | I12N | Q121P | + | random mutant |
| 41 | 15M,I16T | NA | + | random mutant |
| 43 | I16N | T134S, K164I, Q186L, N210S | + | random mutant |
| 10PP | I9N, K27R | NA[d] | + | random mutant |
| 18PP | L13P | NA | + | random mutant |
| LZ12V | I12V | Deletion of aa 1-112 | + | PCR; random |

TABLE 2-continued

Mutations present in the CD40 ligand/zipper domain fusion protein

| Mutant No.: | Zipper Domain Mutation[a] | CD40L Domain Mutations[b] | Activity | Type of Mutant |
|---|---|---|---|---|

[a]Mutations are given as the residue present in the native peptide, the residue number, and the residue present in the mutein. Residue numbers for zipper domain mutations are relative to SEQ ID NO:2.
[b]Residue numbers for mutations in the CD40L domain are relative to SEQ ID NO:4.
[c]Mutant 10PP also contained mutations in regions other than CD40L domain or the zipper domain (T-4S, D-2P, relative to SEQ ID NO:11).
[d]Not applicable Mutant 18PP had only a single mutation in the molecule, which was sufficient to affect secretion in yeast. Mutant 41 had two mutations, both of which were in the isoleucine residues of the zipper domain. The mutations in the zipper improve secretion from yeast without apparent effect on activity.

Additional constructs were prepared by substituting the lung surfactant protein D (SPD) trimerization domain (SEQ ID NO:9; Hoppe, et al., *FEBS Letters* 344:191, 1994) in place of the trimer-forming zipper of SEQ ID NO:2. This construct was expressed in *S. cerevisiae* at low levels. Activity is determined as described previously; various constructs can also be prepared to optimize secretion or other product characteristics.

What is claimed is:

1. A method of preparing a soluble, oligomeric protein by culturing a host cell transformed or transfected with an expression vector encoding a fusion protein comprising a leucine zipper selected from the group consisting of a peptide comprising amino acids 1 through 33 of SEQ ID NO:2, a peptide comprising amino acids 1 through 27 of SEQ ID NO:9, fragments of the peptides having an amino acid sequence set forth in SEQ ID NOs:2 or 9, and peptides having an amino acid sequence as set forth in SEO ID. NOs:2 or 9 except for conservative amino acid substitutions, wherein the peptide or the fragments thereof trimerizes in solution, and an extracellular region of a heterologous mammalian transmembrane protein, wherein when the transmembrane protein is a type II transmembrane protein, the zipper domain is fused to the amino-proximal end of the extracellular region, and when the transmembrane protein is a type I transmembrane protein, the zipper domain is fused to the carboxy-proximal end of the extracellular region, under conditions promoting expression of the fusion protein, and recovering the soluble, oligomeric protein comprising said fusion protein.

2. The method according to claim 1, wherein the fusion protein further comprises a linker sequence.

3. A soluble, oligomeric protein comprising a leucine zipper selected from the group consisting of a peptide-comprising amino acids 1 through 33 of SEQ ID NO:2, a peptide comprising amino acids 1 through 27 of SEQ ID NO:9, fragments of the peptides having an amino acid sequence set forth in SEQ ID NOs:2 or 9, and peptides having an amino acid sequence as set forth in SEQ ID NOs:2 or 9 except for conservative amino acid substitutions, wherein the peptide or the fragments thereof trimerizes in solution, and an extracellular region of a heterologous mammalian transmembrane protein, wherein when the transmembrane protein is a type II transmembrane protein, the zipper domain is fused to the amino-proximal end of the extracellular region, and when the transmembrane protein is a type I transmembrane protein, the zipper domain is fused to the carboxy-proximal end of the extracellular region.

4. The soluble, oligomeric protein according to claim 3, wherein the fusion protein further comprises a linker sequence.

5. A DNA encoding a soluble, oligomeric protein according to claim 3.

6. A DNA encoding a soluble, oligomeric protein according to claim 4.

7. The method according to claim 1, wherein the leucine zipper is selected from the group consisting of a peptide comprising amino acids 1 through 33 of SEQ ID NO:2, fragments of the peptide of SEQ ID NO:2 that trimerize in solution, and peptides having an amino acid sequence as set forth in SEQ ID NO:2 except for conservative amino acid substitutions, and that trimerize in solution.

8. The method according to claim 7, wherein the soluble, oligomeric fusion protein further comprises a linker peptide.

9. The soluble oligomeric fusion protein according to claim 3, wherein the leucine zipper is selected from the group consisting of a peptide comprising amino acids 1 through 33 of SEQ ID NO:2, fragments of the peptide of SEQ ID NO: 2 that trimerize in solution, and peptides having an amino acid sequence as set forth in SEQ ID NO: 2 except for conservative amino acid substitutions, and that trimerize in solution.

10. The soluble oligomeric fusion protein according to claim 9, wherein the soluble, oligomeric fusion protein further comprises a linker peptide.

11. A DNA encoding a soluble, oligomeric protein according to claim 9.

12. The DNA according to claim 11, wherein the DNA encodes a fusion protein further comprising a linker peptide.

13. The method according to claim 7, wherein the peptide has one or more amino acid substitutions selected from the group consisting of Asn for Ile at amino acid 12 of SEQ ID NO:2, Pro for Leu at amino acid 13 of SEQ ID NO:2, Met for Ile at amino acid 5 of SEQ ID NO:2, Thr for Ile at amino acid 16 of SEQ ID NO:2, Asu for Ile at amino acid 16 of SEQ ID NO:2, Asn for Ile at amino acid 9 of SEQ ID NO:2, Arg for Lys at amino acid 27 of SEQ ID NO:2, Val for Ile at amino acid 12 of SEQ ID NO:2.

14. The soluble oligomeric fusion protein according to claim 9, wherein the peptide has one or more amino acid substitutions selected from the group consisting of Asn for Ile at amino acid 12 of SEQ ID NO:2, Pro for Leu at amino acid 13 of SEQ ID NO:2, Met for Ile at amino acid 5 of SEQ ID NO:2, Thr for Ile at amino acid 16 of SEQ ID NO:2, Asn for Ile at amino acid 16 of SEQ ID NO:2, Asn for Ile at amino acid 9 of SEQ ID NO:2, Arg for Lys at amino acid 27 of SEQ ID NO:2, Val for Ile at amino acid 12 of SEQ ID NO:2.

15. The DNA according to claim 11, wherein DNA encodes a peptide having one or more amino acid substitutions selected from the group consisting of Asn for Ile at amino acid 12 of SEQ ID NO:2, Pro for Leu at amino acid 13 of SEQ ID NO:2, Met for Ile at amino acid 5 of SEQ ID NO:2, Thr for Ile at amino acid 16 of SEQ ID NO:2, Asn for Ile at amino acid 16 of SEQ ID NO:2, Asn for Ile at amino acid 9 of SEQ ID NO:2, Arg for Lys at amino acid 27 of SEQ ID NO:2, Val for Ile at amino acid 12 of SEQ ID NO:2.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
Asp  Tyr  Lys  Asp  Asp  Asp  Asp  Lys
1                   5
```

( 2 ) INFORMATION FOR SEQ ID NO:2:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Arg  Met  Lys  Gln  Ile  Glu  Asp  Lys  Ile  Glu  Glu  Ile  Leu  Ser  Lys  Ile
1                   5                        10                       15

Tyr  His  Ile  Glu  Asn  Glu  Ile  Ala  Arg  Ile  Lys  Lys  Leu  Ile  Gly  Glu
                    20                       25                       30

Arg
```

( 2 ) INFORMATION FOR SEQ ID NO:3:

( i ) SEQUENCE CHARACTERISTICS:
        ( A ) LENGTH: 786 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
  ( A ) ORGANISM: Human
  ( B ) STRAIN: CD40-L ( i x ) FEATURE:
  ( A ) NAME/KEY: CDS
  ( B ) LOCATION: 1..783

( x i ) SEQUENCE DESCRIPTION: SEQ ID NO:3:

```
ATG ATC GAA ACA TAC AAC CAA ACT TCT CCC CGA TCT GCG GCC ACT GGA       48
Met Ile Glu Thr Tyr Asn Gln Thr Ser Pro Arg Ser Ala Ala Thr Gly
 1               5                  10                  15

CTG CCC ATC AGC ATG AAA ATT TTT ATG TAT TTA CTT ACT GTT TTT CTT       96
Leu Pro Ile Ser Met Lys Ile Phe Met Tyr Leu Leu Thr Val Phe Leu
             20                  25                  30

ATC ACC CAG ATG ATT GGG TCA GCA CTT TTT GCT GTG TAT CTT CAT AGA      144
Ile Thr Gln Met Ile Gly Ser Ala Leu Phe Ala Val Tyr Leu His Arg
         35                  40                  45

AGG TTG GAC AAG ATA GAA GAT GAA AGG AAT CTT CAT GAA GAT TTT GTA      192
Arg Leu Asp Lys Ile Glu Asp Glu Arg Asn Leu His Glu Asp Phe Val
     50                  55                  60

TTC ATG AAA ACG ATA CAG AGA TGC AAC ACA GGA GAA AGA TCC TTA TCC      240
Phe Met Lys Thr Ile Gln Arg Cys Asn Thr Gly Glu Arg Ser Leu Ser
 65                  70                  75                  80

TTA CTG AAC TGT GAG GAG ATT AAA AGC CAG TTT GAA GGC TTT GTG AAG      288
Leu Leu Asn Cys Glu Glu Ile Lys Ser Gln Phe Glu Gly Phe Val Lys
                 85                  90                  95

GAT ATA ATG TTA AAC AAA GAG GAG ACG AAG AAA GAA AAC AGC TTT GAA      336
Asp Ile Met Leu Asn Lys Glu Glu Thr Lys Lys Glu Asn Ser Phe Glu
            100                 105                 110

ATG CAA AAA GGT GAT CAG AAT CCT CAA ATT GCG GCA CAT GTC ATA AGT      384
Met Gln Lys Gly Asp Gln Asn Pro Gln Ile Ala Ala His Val Ile Ser
        115                 120                 125

GAG GCC AGC AGT AAA ACA ACA TCT GTG TTA CAG TGG GCT GAA AAA GGA      432
Glu Ala Ser Ser Lys Thr Thr Ser Val Leu Gln Trp Ala Glu Lys Gly
    130                 135                 140

TAC TAC ACC ATG AGC AAC AAC TTG GTA ACC CTG GAA AAT GGG AAA CAG      480
Tyr Tyr Thr Met Ser Asn Asn Leu Val Thr Leu Glu Asn Gly Lys Gln
145                 150                 155                 160

CTG ACC GTT AAA AGA CAA GGA CTC TAT TAT ATC TAT GCC CAA GTC ACC      528
Leu Thr Val Lys Arg Gln Gly Leu Tyr Tyr Ile Tyr Ala Gln Val Thr
                165                 170                 175

TTC TGT TCC AAT CGG GAA GCT TCG AGT CAA GCT CCA TTT ATA GCC AGC      576
Phe Cys Ser Asn Arg Glu Ala Ser Ser Gln Ala Pro Phe Ile Ala Ser
            180                 185                 190

CTC TGC CTA AAG TCC CCC GGT AGA TTC GAG AGA ATC TTA CTC AGA GCT      624
Leu Cys Leu Lys Ser Pro Gly Arg Phe Glu Arg Ile Leu Leu Arg Ala
        195                 200                 205

GCA AAT ACC CAC AGT TCC GCC AAA CCT TGC GGG CAA CAA TCC ATT CAC      672
Ala Asn Thr His Ser Ser Ala Lys Pro Cys Gly Gln Gln Ser Ile His
    210                 215                 220

TTG GGA GGA GTA TTT GAA TTG CAA CCA GGT GCT TCG GTG TTT GTC AAT      720
Leu Gly Gly Val Phe Glu Leu Gln Pro Gly Ala Ser Val Phe Val Asn
225                 230                 235                 240

GTG ACT GAT CCA AGC CAA GTG AGC CAT GGC ACT GGC TTC ACG TCC TTT      768
Val Thr Asp Pro Ser Gln Val Ser His Gly Thr Gly Phe Thr Ser Phe
                245                 250                 255

GGC TTA CTC AAA CTC TGA                                              786
```

Gly Leu Leu Lys Leu
                260

( 2 ) INFORMATION FOR SEQ ID NO:4:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Met Ile Glu Thr Tyr Asn Gln Thr Ser Pro Arg Ser Ala Ala Thr Gly
 1               5                  10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
               100                 105                 110

Met Gln Lys Gly Asp Gln Asn Pro Gln Ile Ala Ala His Val Ile Ser
           115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
                260

( 2 ) INFORMATION FOR SEQ ID NO:5:

( i ) SEQUENCE CHARACTERISTICS:
        ( A ) LENGTH: 783 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
  ( A ) ORGANISM: Mouse
  ( B ) STRAIN: CD40-L ( i x ) FEATURE:
  ( A ) NAME/KEY: CDS
  ( B ) LOCATION: 1..780

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| ATG | ATA | GAA | ACA | TAC | AGC | CAA | CCT | TCC | CCC | AGA | TCC | GTG | GCA | ACT | GGA | 48 |
| Met | Ile | Glu | Thr | Tyr | Ser | Gln | Pro | Ser | Pro | Arg | Ser | Val | Ala | Thr | Gly | |
| 1 | | | | 5 | | | | | 10 | | | | | 15 | | |
| CTT | CCA | GCG | AGC | ATG | AAG | ATT | TTT | ATG | TAT | TTA | CTT | ACT | GTT | TTC | CTT | 96 |
| Leu | Pro | Ala | Ser | Met | Lys | Ile | Phe | Met | Tyr | Leu | Leu | Thr | Val | Phe | Leu | |
| | | | 20 | | | | | 25 | | | | | 30 | | | |
| ATC | ACC | CAA | ATG | ATT | GGA | TCT | GTG | CTT | TTT | GCT | GTG | TAT | CTT | CAT | AGA | 144 |
| Ile | Thr | Gln | Met | Ile | Gly | Ser | Val | Leu | Phe | Ala | Val | Tyr | Leu | His | Arg | |
| | | | 35 | | | | | 40 | | | | | 45 | | | |
| AGA | TTG | GAT | AAG | GTC | GAA | GAG | GAA | GTA | AAC | CTT | CAT | GAA | GAT | TTT | GTA | 192 |
| Arg | Leu | Asp | Lys | Val | Glu | Glu | Glu | Val | Asn | Leu | His | Glu | Asp | Phe | Val | |
| | | 50 | | | | | 55 | | | | | 60 | | | | |
| TTC | ATA | AAA | AAG | CTA | AAG | AGA | TGC | AAC | AAA | GGA | GAA | GGA | TCT | TTA | TCC | 240 |
| Phe | Ile | Lys | Lys | Leu | Lys | Arg | Cys | Asn | Lys | Gly | Glu | Gly | Ser | Leu | Ser | |
| 65 | | | | | 70 | | | | | 75 | | | | | 80 | |
| TTG | CTG | AAC | TGT | GAG | GAG | ATG | AGA | AGG | CAA | TTT | GAA | GAC | CTT | GTC | AAG | 288 |
| Leu | Leu | Asn | Cys | Glu | Glu | Met | Arg | Arg | Gln | Phe | Glu | Asp | Leu | Val | Lys | |
| | | | | 85 | | | | | 90 | | | | | 95 | | |
| GAT | ATA | ACG | TTA | AAC | AAA | GAA | GAG | AAA | AAA | GAA | AAC | AGC | TTT | GAA | ATG | 336 |
| Asp | Ile | Thr | Leu | Asn | Lys | Glu | Glu | Lys | Lys | Glu | Asn | Ser | Phe | Glu | Met | |
| | | | 100 | | | | | 105 | | | | | 110 | | | |
| CAA | AGA | GGT | GAT | GAG | GAT | CCT | CAA | ATT | GCA | GCA | CAC | GTT | GTA | AGC | GAA | 384 |
| Gln | Arg | Gly | Asp | Glu | Asp | Pro | Gln | Ile | Ala | Ala | His | Val | Val | Ser | Glu | |
| | | 115 | | | | | 120 | | | | | 125 | | | | |
| GCC | AAC | AGT | AAT | GCA | GCA | TCC | GTT | CTA | CAG | TGG | GCC | AAG | AAA | GGA | TAT | 432 |
| Ala | Asn | Ser | Asn | Ala | Ala | Ser | Val | Leu | Gln | Trp | Ala | Lys | Lys | Gly | Tyr | |
| | | 130 | | | | | 135 | | | | | 140 | | | | |
| TAT | ACC | ATG | AAA | AGC | AAC | TTG | GTA | ATG | CTT | GAA | AAT | GGG | AAA | CAG | CTG | 480 |
| Tyr | Thr | Met | Lys | Ser | Asn | Leu | Val | Met | Leu | Glu | Asn | Gly | Lys | Gln | Leu | |
| 145 | | | | | 150 | | | | | 155 | | | | | 160 | |
| ACG | GTT | AAA | AGA | GAA | GGA | CTC | TAT | TAT | GTC | TAC | ACT | CAA | GTC | ACC | TTC | 528 |
| Thr | Val | Lys | Arg | Glu | Gly | Leu | Tyr | Tyr | Val | Tyr | Thr | Gln | Val | Thr | Phe | |
| | | | | 165 | | | | | 170 | | | | | 175 | | |
| TGC | TCT | AAT | CGG | GAG | CCT | TCG | AGT | CAA | CGC | CCA | TTC | ATC | GTC | GGC | CTC | 576 |
| Cys | Ser | Asn | Arg | Glu | Pro | Ser | Ser | Gln | Arg | Pro | Phe | Ile | Val | Gly | Leu | |
| | | | 180 | | | | | 185 | | | | | 190 | | | |
| TGG | CTG | AAG | CCC | AGC | AGT | GGA | TCT | GAG | AGA | ATC | TTA | CTC | AAG | GCG | GCA | 624 |
| Trp | Leu | Lys | Pro | Ser | Ser | Gly | Ser | Glu | Arg | Ile | Leu | Leu | Lys | Ala | Ala | |
| | | | 195 | | | | | 200 | | | | | 205 | | | |
| AAT | ACC | CAC | AGT | TCC | TCC | CAG | CTT | TGC | GAG | CAG | CAG | TCT | GTT | CAC | TTG | 672 |
| Asn | Thr | His | Ser | Ser | Ser | Gln | Leu | Cys | Glu | Gln | Gln | Ser | Val | His | Leu | |
| | 210 | | | | | 215 | | | | | 220 | | | | | |
| GGC | GGA | GTG | TTT | GAA | TTA | CAA | GCT | GGT | GCT | TCT | GTG | TTT | GTC | AAC | GTG | 720 |
| Gly | Gly | Val | Phe | Glu | Leu | Gln | Ala | Gly | Ala | Ser | Val | Phe | Val | Asn | Val | |
| 225 | | | | | 230 | | | | | 235 | | | | | 240 | |
| ACT | GAA | GCA | AGC | CAA | GTG | ATC | CAC | AGA | GTT | GGC | TTC | TCA | TCT | TTT | GGC | 768 |
| Thr | Glu | Ala | Ser | Gln | Val | Ile | His | Arg | Val | Gly | Phe | Ser | Ser | Phe | Gly | |
| | | | | 245 | | | | | 250 | | | | | 255 | | |
| TTA | CTC | AAA | CTC | TGA | | | | | | | | | | | | 783 |
| Leu | Leu | Lys | Leu | | | | | | | | | | | | | |
| | | | 260 | | | | | | | | | | | | | |

( 2 ) INFORMATION FOR SEQ ID NO:6:

( i ) SEQUENCE CHARACTERISTICS:
        ( A ) LENGTH: 260 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ile  Glu  Thr  Tyr  Ser  Gln  Pro  Ser  Pro  Arg  Ser  Val  Ala  Thr  Gly
 1              5                   10                      15
Leu  Pro  Ala  Ser  Met  Lys  Ile  Phe  Met  Tyr  Leu  Leu  Thr  Val  Phe  Leu
              20                   25                      30
Ile  Thr  Gln  Met  Ile  Gly  Ser  Val  Leu  Phe  Ala  Val  Tyr  Leu  His  Arg
         35                  40                       45
Arg  Leu  Asp  Lys  Val  Glu  Glu  Val  Asn  Leu  His  Glu  Asp  Phe  Val
     50                   55                  60
Phe  Ile  Lys  Lys  Leu  Lys  Arg  Cys  Asn  Lys  Gly  Glu  Gly  Ser  Leu  Ser
 65                       70                  75                           80
Leu  Leu  Asn  Cys  Glu  Glu  Met  Arg  Arg  Gln  Phe  Glu  Asp  Leu  Val  Lys
                   85                   90                       95
Asp  Ile  Thr  Leu  Asn  Lys  Glu  Glu  Lys  Lys  Glu  Asn  Ser  Phe  Glu  Met
              100                  105                      110
Gln  Arg  Gly  Asp  Glu  Asp  Pro  Gln  Ile  Ala  Ala  His  Val  Val  Ser  Glu
              115                  120                      125
Ala  Asn  Ser  Asn  Ala  Ala  Ser  Val  Leu  Gln  Trp  Ala  Lys  Lys  Gly  Tyr
     130                  135                      140
Tyr  Thr  Met  Lys  Ser  Asn  Leu  Val  Met  Leu  Glu  Asn  Gly  Lys  Gln  Leu
145                       150                      155                       160
Thr  Val  Lys  Arg  Glu  Gly  Leu  Tyr  Tyr  Val  Tyr  Thr  Gln  Val  Thr  Phe
              165                      170                       175
Cys  Ser  Asn  Arg  Glu  Pro  Ser  Ser  Gln  Arg  Pro  Phe  Ile  Val  Gly  Leu
              180                  185                      190
Trp  Leu  Lys  Pro  Ser  Ser  Gly  Ser  Glu  Arg  Ile  Leu  Leu  Lys  Ala  Ala
          195                  200                      205
Asn  Thr  His  Ser  Ser  Ser  Gln  Leu  Cys  Glu  Gln  Gln  Ser  Val  His  Leu
     210                       215                  220
Gly  Gly  Val  Phe  Glu  Leu  Gln  Ala  Gly  Ala  Ser  Val  Phe  Val  Asn  Val
225                       230                      235                       240
Thr  Glu  Ala  Ser  Gln  Val  Ile  His  Arg  Val  Gly  Phe  Ser  Ser  Phe  Gly
                   245                       250                      255
Leu  Leu  Lys  Leu
              260
```

( 2 ) INFORMATION FOR SEQ ID NO:7:

( i ) SEQUENCE CHARACTERISTICS:
        ( A ) LENGTH: 689 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: CD27 ligand trimer (CD27L-3)

( i x ) FEATURE:
    ( A ) NAME/KEY: CDS
    ( B ) LOCATION: 39..686

( i x ) FEATURE:
    ( A ) NAME/KEY: sig_peptide
    ( B ) LOCATION: 39..110

( i x ) FEATURE:
    ( A ) NAME/KEY: mat_peptide
    ( B ) LOCATION: 111..686

( x i ) SEQUENCE DESCRIPTION: SEQ ID NO:7:

```
GGAAAACTCT CGAGGTACCT ATCCCGGGGA TCCCCACC ATG TTC CAT GTC TCT                53
                                           Met Phe His Val Ser
                                           -24              -20

TTT AGA TAT ATC TTT GGA ATT CCT CCA CTG ATC CTT GTT CTG CTG CCT             101
Phe Arg Tyr Ile Phe Gly Ile Pro Pro Leu Ile Leu Val Leu Leu Pro
            -15                 -10                          -5

GTC ACT AGT TCT GAC CGT ATG AAA CAG ATA GAG GAT AAG ATC GAA GAG             149
Val Thr Ser Ser Asp Arg Met Lys Gln Ile Glu Asp Lys Ile Glu Glu
                1               5                   10

ATC CTA AGT AAG ATT TAT CAT ATA GAG AAT GAA ATC GCC CGT ATC AAA             197
Ile Leu Ser Lys Ile Tyr His Ile Glu Asn Glu Ile Ala Arg Ile Lys
        15              20                  25

AAG CTG ATT GGC GAG CGG ACT AGT CAG CGC TTC GCA CAG GCT CAG CAG             245
Lys Leu Ile Gly Glu Arg Thr Ser Gln Arg Phe Ala Gln Ala Gln Gln
30              35                  40                      45

CAG CTG CCG CTC GAG TCA CTT GGG TGG GAC GTA GCT GAG CTG CAG CTG             293
Gln Leu Pro Leu Glu Ser Leu Gly Trp Asp Val Ala Glu Leu Gln Leu
                50                  55                  60

AAT CAC ACA GGA CCT CAG CAG GAC CCC AGG CTA TAC TGG CAG GGG GGC             341
Asn His Thr Gly Pro Gln Gln Asp Pro Arg Leu Tyr Trp Gln Gly Gly
            65              70                  75

CCA GCA CTG GGC CGC TCC TTC CTG CAT GGA CCA GAG CTG GAC AAG GGG             389
Pro Ala Leu Gly Arg Ser Phe Leu His Gly Pro Glu Leu Asp Lys Gly
        80              85                  90

CAG CTA CGT ATC CAT CGT GAT GGC ATC TAC ATG GTA CAC ATC CAG GTG             437
Gln Leu Arg Ile His Arg Asp Gly Ile Tyr Met Val His Ile Gln Val
95              100                 105

ACG CTG GCC ATC TGC TCC TCC ACG ACG GCC TCC AGG CAC CAC CCC ACC             485
Thr Leu Ala Ile Cys Ser Ser Thr Thr Ala Ser Arg His His Pro Thr
110             115                 120                     125

ACC CTG GCC GTG GGA ATC TGC TCT CCC GCC TCC CGT AGC ATC AGC CTG             533
Thr Leu Ala Val Gly Ile Cys Ser Pro Ala Ser Arg Ser Ile Ser Leu
                130                 135                 140

CTG CGT CTC AGC TTC CAC CAA GGT TGT ACC ATT GTC TCC CAG CGC CTG             581
Leu Arg Leu Ser Phe His Gln Gly Cys Thr Ile Val Ser Gln Arg Leu
            145                 150                 155

ACG CCC CTG GCC CGA GGG GAC ACA CTC TGC ACC AAC CTC ACT GGG ACA             629
Thr Pro Leu Ala Arg Gly Asp Thr Leu Cys Thr Asn Leu Thr Gly Thr
        160                 165                 170

CTT TTG CCT TCC CGA AAC ACT GAT GAG ACC TTC TTT GGA GTG CAG TGG             677
Leu Leu Pro Ser Arg Asn Thr Asp Glu Thr Phe Phe Gly Val Gln Trp
175                 180                 185

GTG CGC CCC TGA                                                             689
Val Arg Pro
190
```

( 2 ) INFORMATION FOR SEQ ID NO:8:

( i ) SEQUENCE CHARACTERISTICS:
        ( A ) LENGTH: 216 amino acids
        ( B ) TYPE: amino acid (D) TOPOLOGY: linear (ii) MOLECULE TYPE: protein (xi) SEQUENCE DESCRIPTION: SEQ ID NO:8:

| Met | Phe | His | Val | Ser | Phe | Arg | Tyr | Ile | Phe | Gly | Ile | Pro | Pro | Leu | Ile |
|-----|-----|-----|-----|-----|-----|-----|-----|-----|-----|-----|-----|-----|-----|-----|-----|
| -24 |     |     |     | -20 |     |     |     |     | -15 |     |     |     |     | -10 |     |

| Leu | Val | Leu | Leu | Pro | Val | Thr | Ser | Ser | Asp | Arg | Met | Lys | Gln | Ile | Glu |
|-----|-----|-----|-----|-----|-----|-----|-----|-----|-----|-----|-----|-----|-----|-----|-----|
|     |     |     | -5  |     |     |     |     | 1   |     |     |     | 5   |     |     |     |

| Asp | Lys | Ile | Glu | Glu | Ile | Leu | Ser | Lys | Ile | Tyr | His | Ile | Glu | Asn | Glu |
|-----|-----|-----|-----|-----|-----|-----|-----|-----|-----|-----|-----|-----|-----|-----|-----|
|     | 10  |     |     |     |     | 15  |     |     |     |     | 20  |     |     |     |     |

| Ile | Ala | Arg | Ile | Lys | Lys | Leu | Ile | Gly | Glu | Arg | Thr | Ser | Gln | Arg | Phe |
|-----|-----|-----|-----|-----|-----|-----|-----|-----|-----|-----|-----|-----|-----|-----|-----|
| 25  |     |     |     |     | 30  |     |     |     |     | 35  |     |     |     |     | 40  |

| Ala | Gln | Ala | Gln | Gln | Gln | Leu | Pro | Leu | Glu | Ser | Leu | Gly | Trp | Asp | Val |
|-----|-----|-----|-----|-----|-----|-----|-----|-----|-----|-----|-----|-----|-----|-----|-----|
|     |     |     |     | 45  |     |     |     |     | 50  |     |     |     |     | 55  |     |

| Ala | Glu | Leu | Gln | Leu | Asn | His | Thr | Gly | Pro | Gln | Gln | Asp | Pro | Arg | Leu |
|-----|-----|-----|-----|-----|-----|-----|-----|-----|-----|-----|-----|-----|-----|-----|-----|
|     |     |     | 60  |     |     |     |     | 65  |     |     |     |     | 70  |     |     |

| Tyr | Trp | Gln | Gly | Gly | Pro | Ala | Leu | Gly | Arg | Ser | Phe | Leu | His | Gly | Pro |
|-----|-----|-----|-----|-----|-----|-----|-----|-----|-----|-----|-----|-----|-----|-----|-----|
|     |     | 75  |     |     |     |     | 80  |     |     |     |     | 85  |     |     |     |

| Glu | Leu | Asp | Lys | Gly | Gln | Leu | Arg | Ile | His | Arg | Asp | Gly | Ile | Tyr | Met |
|-----|-----|-----|-----|-----|-----|-----|-----|-----|-----|-----|-----|-----|-----|-----|-----|
|     | 90  |     |     |     |     | 95  |     |     |     |     | 100 |     |     |     |     |

| Val | His | Ile | Gln | Val | Thr | Leu | Ala | Ile | Cys | Ser | Ser | Thr | Thr | Ala | Ser |
|-----|-----|-----|-----|-----|-----|-----|-----|-----|-----|-----|-----|-----|-----|-----|-----|
| 105 |     |     |     |     | 110 |     |     |     |     | 115 |     |     |     |     | 120 |

| Arg | His | His | Pro | Thr | Thr | Leu | Ala | Val | Gly | Ile | Cys | Ser | Pro | Ala | Ser |
|-----|-----|-----|-----|-----|-----|-----|-----|-----|-----|-----|-----|-----|-----|-----|-----|
|     |     |     |     | 125 |     |     |     |     | 130 |     |     |     |     | 135 |     |

| Arg | Ser | Ile | Ser | Leu | Leu | Arg | Leu | Ser | Phe | His | Gln | Gly | Cys | Thr | Ile |
|-----|-----|-----|-----|-----|-----|-----|-----|-----|-----|-----|-----|-----|-----|-----|-----|
|     |     |     | 140 |     |     |     |     | 145 |     |     |     |     | 150 |     |     |

| Val | Ser | Gln | Arg | Leu | Thr | Pro | Leu | Ala | Arg | Gly | Asp | Thr | Leu | Cys | Thr |
|-----|-----|-----|-----|-----|-----|-----|-----|-----|-----|-----|-----|-----|-----|-----|-----|
|     |     | 155 |     |     |     |     | 160 |     |     |     |     | 165 |     |     |     |

| Asn | Leu | Thr | Gly | Thr | Leu | Leu | Pro | Ser | Arg | Asn | Thr | Asp | Glu | Thr | Phe |
|-----|-----|-----|-----|-----|-----|-----|-----|-----|-----|-----|-----|-----|-----|-----|-----|
|     | 170 |     |     |     |     | 175 |     |     |     |     | 180 |     |     |     |     |

| Phe | Gly | Val | Gln | Trp | Val | Arg | Pro |
|-----|-----|-----|-----|-----|-----|-----|-----|
| 185 |     |     |     |     | 190 |     |     |

(2) INFORMATION FOR SEQ ID NO:9:

(i) SEQUENCE CHARACTERISTICS:
    (A) LENGTH: 27 amino acids
    (B) TYPE: amino acid
    (C) STRANDEDNESS: Not Relevant
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:9:

| Pro | Asp | Val | Ala | Ser | Leu | Arg | Gln | Gln | Val | Glu | Ala | Leu | Gln | Gly | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Gln | His | Leu | Gln | Ala | Ala | Phe | Ser | Gln | Tyr |
|-----|-----|-----|-----|-----|-----|-----|-----|-----|-----|-----|
|     |     |     | 20  |     |     |     |     | 25  |     |     |

(2) INFORMATION FOR SEQ ID NO:10:

(i) SEQUENCE CHARACTERISTICS:
    (A) LENGTH: 929 base pairs
    (B) TYPE: nucleic acid
    (C) STRANDEDNESS: single
    (D) TOPOLOGY: linear ( i i ) MOLECULE TYPE: cDNA ( v i ) ORIGINAL SOURCE:
  ( A ) ORGANISM: Human CD40-L trimer ( i x ) FEATURE:
  ( A ) NAME/KEY: sig_peptide
  ( B ) LOCATION: 65..142

( i x ) FEATURE:
  ( A ) NAME/KEY: CDS
  ( B ) LOCATION: 65..886

( i x ) FEATURE:
  ( A ) NAME/KEY: mat_peptide
  ( B ) LOCATION: 143..886

( x i ) SEQUENCE DESCRIPTION: SEQ ID NO:10:

```
TGAGCGAGTC CGCATCGACG GATCGGAAAA CCTCTCCGAG GTACCTATCC CGGGGATCCC        60

CACC ATG TTC CAT GTT TCT TTT AGA TAT ATC TTT GGA ATT CCT CCA CTG       109
     Met Phe His Val Ser Phe Arg Tyr Ile Phe Gly Ile Pro Pro Leu
     -26 -25              -20                   -15

ATC CTT GTT CTG CTG CCT GTC ACT AGT TCT GAC CGT ATG AAA CAG ATA        157
Ile Leu Val Leu Leu Pro Val Thr Ser Ser Asp Arg Met Lys Gln Ile
-10              -5                    1                        5

GAG GAT AAG ATC GAA GAG ATC CTA AGT AAG ATT TAT CAT ATA GAG AAT        205
Glu Asp Lys Ile Glu Glu Ile Leu Ser Lys Ile Tyr His Ile Glu Asn
              10                  15                  20

GAA ATC GCC CGT ATC AAA AAG CTG ATT GGC GAG CGG ACT AGT TCT GAC        253
Glu Ile Ala Arg Ile Lys Lys Leu Ile Gly Glu Arg Thr Ser Ser Asp
             25                  30                  35

AAG ATA GAA GAT GAA AGG AAT CTT CAT GAA GAT TTT GTA TTC ATG AAA        301
Lys Ile Glu Asp Glu Arg Asn Leu His Glu Asp Phe Val Phe Met Lys
        40                  45                  50

ACG ATA CAG AGA TGC AAC ACA GGA GAA AGA TCC TTA TCC TTA CTG AAC        349
Thr Ile Gln Arg Cys Asn Thr Gly Glu Arg Ser Leu Ser Leu Leu Asn
   55                  60                  65

TGT GAG GAG ATT AAA AGC CAG TTT GAA GGC TTT GTG AAG GAT ATA ATG        397
Cys Glu Glu Ile Lys Ser Gln Phe Glu Gly Phe Val Lys Asp Ile Met
70                  75                  80                  85

TTA AAC AAA GAG GAG ACG AAG AAA GAA AAC AGC TTT GAA ATG CAA AAA        445
Leu Asn Lys Glu Glu Thr Lys Lys Glu Asn Ser Phe Glu Met Gln Lys
                90                  95                  100

GGT GAT CAG AAT CCT CAA ATT GCG GCA CAT GTC ATA AGT GAG GCC AGC        493
Gly Asp Gln Asn Pro Gln Ile Ala Ala His Val Ile Ser Glu Ala Ser
            105                 110                 115

AGT AAA ACA ACA TCT GTG TTA CAG TGG GCT GAA AAA GGA TAC TAC ACC        541
Ser Lys Thr Thr Ser Val Leu Gln Trp Ala Glu Lys Gly Tyr Tyr Thr
        120                 125                 130

ATG AGC AAC AAC TTG GTA ACC CTG GAA AAT GGG AAA CAG CTG ACC GTT        589
Met Ser Asn Asn Leu Val Thr Leu Glu Asn Gly Lys Gln Leu Thr Val
    135                 140                 145

AAA AGA CAA GGA CTC TAT TAT ATC TAT GCC CAA GTC ACC TTC TGT TCC        637
Lys Arg Gln Gly Leu Tyr Tyr Ile Tyr Ala Gln Val Thr Phe Cys Ser
150                 155                 160                 165

AAT CGG GAA GCT TCG AGT CAA GCT CCA TTT ATA GCC AGC CTC TGC CTA        685
Asn Arg Glu Ala Ser Ser Gln Ala Pro Phe Ile Ala Ser Leu Cys Leu
            170                 175                 180

AAG TCC CCC GGT AGA TTC GAG AGA ATC TTA CTC AGA GCT GCA AAT ACC        733
Lys Ser Pro Gly Arg Phe Glu Arg Ile Leu Leu Arg Ala Ala Asn Thr
        185                 190                 195

CAC AGT TCC GCC AAA CCT TGC GGG CAA CAA TCC ATT CAC TTG GGA GGA        781
His Ser Ser Ala Lys Pro Cys Gly Gln Gln Ser Ile His Leu Gly Gly
    200                 205                 210
```

```
GTA  TTT  GAA  TTG  CAA  CCA  GGT  GCT  TCG  GTG  TTT  GTC  AAT  GTG  ACT  GAT       829
Val  Phe  Glu  Leu  Gln  Pro  Gly  Ala  Ser  Val  Phe  Val  Asn  Val  Thr  Asp
215                      220                      225

CCA  AGC  CAA  GTG  AGC  CAT  GGC  ACT  GGC  TTC  ACG  TCC  TTT  GGC  TTA  CTC       877
Pro  Ser  Gln  Val  Ser  His  Gly  Thr  Gly  Phe  Thr  Ser  Phe  Gly  Leu  Leu
230                      235                      240                      245

AAA  CTC  TGAGCGGCCG  CTACAGATGA  ATAATAAGCA  TGTTTGGATT  CCTCAA                     929
Lys  Leu
```

( 2 ) INFORMATION FOR SEQ ID NO:11:

( i ) SEQUENCE CHARACTERISTICS:
        ( A ) LENGTH: 273 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Phe  His  Val  Ser  Phe  Arg  Tyr  Ile  Phe  Gly  Ile  Pro  Pro  Leu  Ile
-26  -25                 -20                 -15

Leu  Val  Leu  Leu  Pro  Val  Thr  Ser  Ser  Asp  Arg  Met  Lys  Gln  Ile  Glu
-10                  -5                        1                        5

Asp  Lys  Ile  Glu  Glu  Ile  Leu  Ser  Lys  Ile  Tyr  His  Ile  Glu  Asn  Glu
               10                  15                       20

Ile  Ala  Arg  Ile  Lys  Lys  Leu  Ile  Gly  Glu  Arg  Thr  Ser  Ser  Asp  Lys
          25                       30                       35

Ile  Glu  Asp  Glu  Arg  Asn  Leu  His  Glu  Asp  Phe  Val  Phe  Met  Lys  Thr
40                            45                      50

Ile  Gln  Arg  Cys  Asn  Thr  Gly  Glu  Arg  Ser  Leu  Ser  Leu  Leu  Asn  Cys
55                       60                      65                           70

Glu  Glu  Ile  Lys  Ser  Gln  Phe  Glu  Gly  Phe  Val  Lys  Asp  Ile  Met  Leu
                    75                      80                            85

Asn  Lys  Glu  Glu  Thr  Lys  Lys  Glu  Asn  Ser  Phe  Glu  Met  Gln  Lys  Gly
               90                      95                      100

Asp  Gln  Asn  Pro  Gln  Ile  Ala  Ala  His  Val  Ile  Ser  Glu  Ala  Ser  Ser
          105                      110                      115

Lys  Thr  Thr  Ser  Val  Leu  Gln  Trp  Ala  Glu  Lys  Gly  Tyr  Tyr  Thr  Met
120                           125                      130

Ser  Asn  Asn  Leu  Val  Thr  Leu  Glu  Asn  Gly  Lys  Gln  Leu  Thr  Val  Lys
135                      140                      145                      150

Arg  Gln  Gly  Leu  Tyr  Tyr  Ile  Tyr  Ala  Gln  Val  Thr  Phe  Cys  Ser  Asn
               155                      160                      165

Arg  Glu  Ala  Ser  Ser  Gln  Ala  Pro  Phe  Ile  Ala  Ser  Leu  Cys  Leu  Lys
               170                      175                      180

Ser  Pro  Gly  Arg  Phe  Glu  Arg  Ile  Leu  Leu  Arg  Ala  Ala  Asn  Thr  His
               185                      190                      195

Ser  Ser  Ala  Lys  Pro  Cys  Gly  Gln  Gln  Ser  Ile  His  Leu  Gly  Gly  Val
          200                      205                      210

Phe  Glu  Leu  Gln  Pro  Gly  Ala  Ser  Val  Phe  Val  Asn  Val  Thr  Asp  Pro
215                      220                      225                      230

Ser  Gln  Val  Ser  His  Gly  Thr  Gly  Phe  Thr  Ser  Phe  Gly  Leu  Leu  Lys
                    235                      240                      245

Leu
```